United States Patent
Subramanian Gopinath et al.

(10) Patent No.: US 11,958,044 B2
(45) Date of Patent: Apr. 16, 2024

(54) THIN FILM BASED PHOTOCATALYST DEVICE FOR HYDROGEN GENERATION AND ALCOHOLS OXIDATION IN DIRECT SUNLIGHT

(71) Applicant: COUNCIL OF SCIENTIFIC AND INDUSTRIAL RESEARCH, New Delhi (IN)

(72) Inventors: Chinnakonda Subramanian Gopinath, Pune (IN); Naresh Nalajala, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 301 days.

(21) Appl. No.: 17/297,592

(22) PCT Filed: Nov. 27, 2019

(86) PCT No.: PCT/IN2019/050867
§ 371 (c)(1),
(2) Date: May 27, 2021

(87) PCT Pub. No.: WO2020/110145
PCT Pub. Date: Jun. 4, 2020

(65) Prior Publication Data
US 2022/0048018 A1    Feb. 17, 2022

(30) Foreign Application Priority Data
Nov. 27, 2018  (IN) .............................. 201811044638

(51) Int. Cl.
*B01J 35/39*    (2024.01)
*B01J 21/06*    (2006.01)
(Continued)

(52) U.S. Cl.
CPC ............. *B01J 35/39* (2024.01); *B01J 21/063* (2013.01); *B01J 21/08* (2013.01); *B01J 23/44* (2013.01);
(Continued)

(58) Field of Classification Search
None
See application file for complete search history.

(56) References Cited

U.S. PATENT DOCUMENTS

2004/0241040 A1* 12/2004 Wei ...................... B01J 35/004
                                                                422/4
2009/0062109 A1*  3/2009 Boyd ..................... B01J 35/004
                                                                502/159
(Continued)

FOREIGN PATENT DOCUMENTS

JP    2018145429 A  *  9/2018
WO    2017118887 A1    7/2017

OTHER PUBLICATIONS

Likius et al, Percolation threshold for electrical resistivity of Ag-nanoparticle/ titania composite thin films fabricated using molecular precursor method, J. Mater. Sci. 47, pp. 3890-3899 (Year: 2012).*
(Continued)

*Primary Examiner* — Stefanie J Cohen
(74) *Attorney, Agent, or Firm* — Workman Nydegger

(57) ABSTRACT

The present invention relates to a photocatalyst device obtained by thin film making on solid surfaces, wherein the device comprises of titania, optionally in the form of composite with noble or transition metal(s) or metal oxides. This device (FIG. 1) is evaluated in direct sunlight for hydrogen generation (FIG. 4) and oxidation of alcohols (Table 3) using aqueous alcohol solution through water splitting and simultaneously oxidizing alcohol to oxygenated products.

16 Claims, 3 Drawing Sheets

(51) Int. Cl.

| | |
|---|---|
| *B01J 21/08* | (2006.01) |
| *B01J 23/44* | (2006.01) |
| *B01J 23/46* | (2006.01) |
| *B01J 23/50* | (2006.01) |
| *B01J 23/52* | (2006.01) |
| *B01J 23/72* | (2006.01) |
| *B01J 23/75* | (2006.01) |
| *B01J 23/755* | (2006.01) |
| *B01J 37/02* | (2006.01) |
| *C01B 3/04* | (2006.01) |
| *C07C 45/29* | (2006.01) |
| *C07C 51/16* | (2006.01) |
| *C03C 17/09* | (2006.01) |

(52) U.S. Cl.
CPC ............. *B01J 23/462* (2013.01); *B01J 23/50* (2013.01); *B01J 23/52* (2013.01); *B01J 23/72* (2013.01); *B01J 23/75* (2013.01); *B01J 23/755* (2013.01); *B01J 37/0234* (2013.01); *C01B 3/042* (2013.01); *C07C 45/29* (2013.01); *C07C 51/16* (2013.01); *C01B 2203/0277* (2013.01); *C01B 2203/1047* (2013.01); *C03C 17/09* (2013.01); *C03C 2217/254* (2013.01); *C03C 2218/15* (2013.01)

(56) References Cited

U.S. PATENT DOCUMENTS

| | | | | |
|---|---|---|---|---|
| 2014/0183141 | A1* | 7/2014 | Kurup | B01J 23/50 252/175 |
| 2014/0296060 | A1* | 10/2014 | Chen | C03C 17/256 502/159 |
| 2016/0193595 | A1* | 7/2016 | Nagpal | B01J 23/72 502/220 |
| 2017/0315436 | A1* | 11/2017 | Yin | G03C 1/732 |
| 2018/0318799 | A1 | 11/2018 | Khan et al. | |

OTHER PUBLICATIONS

JP-2018145429-A- English translation (Year: 2018).*
International Search Report and Written Opinion from PCT/IN2019/050867 filed Nov. 27, 2019, dated Mar. 11, 2020.
Takanabe, Kazuhiro, Photocatalytic Water Splitting: Quantitative Approaches toward Photocatalyst by Design, ACS Catalysis 2017, 7, pp. 8006-8022.
Yamada, Taro et al., Development of Sunlight Driven Water Splitting Devices towards Future Artificial Photosynthetic Industry, Chemengineering, published Aug. 13, 2018, 2, 36, pp. 1-18.
Chiarello, Gian Luca et al. Hydrogen production by photocatalytic steam reforming of methanol on noble metal-modified TiO2, Journal of Catalysis, 273, Jun. 29, 2010, pp. 182-190.
Kitano, Masaaki et al., Decomposition of water in the separate evolution of hydrogen and oxygen using visible light-responsive TiO2 thin film photocatalysts: Effect of the work function of the substrates on the yield of the reaction, Science Direct, Applied Catalyst A: General 314, Sep. 18, 2006, pp. 179-183.

* cited by examiner

THIN FILM BASED PHOTOCATALYST DEVICE FOR HYDROGEN GENERATION AND ALCOHOLS OXIDATION IN DIRECT SUNLIGHT

FIELD OF THE INVENTION

The present invention relates to a photocatalyst device obtained by thin film making on surfaces for the generation of hydrogen and oxygenated products of alcohols in direct sunlight. More particularly, the present invention relates to a photocatalyst device obtained by drop casting method on glass plates, comprises of titania, optionally in the form of composite with noble or transition metal(s) or metal oxides and evaluated for oxygenates and hydrogen generation with an aqueous alcohol substrate.

BACKGROUND AND PRIOR ART

The eventual depletion of fossil fuels in the next few decades, and a daily incremental addition of carbon footprint to the previously crossed danger level (400 ppm $CO_2$ in atmosphere) due to fossil fuel combustion are the two undeniable facts. They necessitate the global community to use renewable resources such as solar, wind, hydel power. $H_2$ is a promising energy carrier with high energy density (141.7 MJ/kg) and zero-emission is definitely advantageous. Although steam reforming of methane is well known to produce $H_2$ at low cost, the environmental hazards due to increasing carbon footprint compel to look for renewable technologies.

The renewable hydrogen production technologies can be classified into three categories, namely, (a) steam reforming of bio derived fuels and hence significantly carbon neutral, (b) electrolytic processes that involves electrolyzer powered from renewable resources (solar, wind etc), and (c) photolytic processes, including photocatalysis or photoelectrocatalysis. Among these, solar driven water splitting reaction with suitable combination of semiconductors and metal nanostructures is preferred, as the method is truly renewable. However, $H_2$ production from particulate form of photocatalyst is hindered by several hurdles.

The article entitled "Photocatalytic water splitting: Quantitative approaches toward photocatalysis by design" by Kazuhiro Takanabe and published in the journal "*ACS Catal.* 2017, 7, 11, 8006-8022" reports different parameters which are responsible for the efficacy of the performance of the photocatalysis reaction and to calculate overall effect of the parameters. It also mentions that thickness of the thin film of the photocatalyst also affects on the results. But, the article shows effect in the context of single crystal thin film.

The article entitled "Decomposition of water in the separate evolution of hydrogen and oxygen using visible light-responsive TiO2 thin film photocatalysts: Effect of the work function of the substrates on the yield of the reaction" by Masaaki Kitano et. al and published in the journal "*Applied Catalysis A: General* 314 (2006) 179-183" reports the development of visible light-responsive $TiO_2$ thin films (vis-$TiO_2$) by applying a radio-frequency magnetron sputtering (RF-MS) deposition method. Catalyst is prepared by deposition method. But, the catalyst of the article do not show significant hydrogen activity as well as RF-Magnetron sputtering have been used to prepare the thin films and it needs to be highlighted that the preparation of thin films demands the use of vacuum and therefore it is very difficult to scale-up making the process very expensive.

The article entitled "Development of Sunlight Driven Water Splitting Devices towards Future Artificial Photosynthetic Industry" by Taro Yamada et. al and published in the journal "*Chem. Engineering,* 2018, 2(3), 36" presents the water splitting devices based on photocatalytic and photoelctrocatalytic devices. In this review, photocatalytic water splitting using RhCrOx/Al:SrTiO3 photocatalyst sheets as thin films over glass plates is described. But, the catalyst do not show significant improvement in hydrogen activity. Therefore, to overcome drawbacks in the prior art there is certainly a need for simple, economical device which will effectively improve the hydrogen activity where the photocatalyst is coated on a fixed substrate (steel, glass plate etc.) to harvest the sunlight.

OBJECTIVE OF THE INVENTION

The main objective of the present invention is to provide photocatalyst thin film devices obtained by simple drop casting or coating method on glass plates, and inner surfaces of glass vessels for hydrogen generation and partial oxidation products of alcohols using water splitting.

SUMMARY OF THE INVENTION

Accordingly, the present invention provides a photocatalyst device obtained by simple drop casting method to prepare thin film on glass plates or coating thin film on the inner surfaces of glass vessels by rota-vapour method for hydrogen generation and partially oxidized product(s) of alcohol using water splitting; wherein said device comprises of (a) a titania photocatayst, optionally in the form of composite with noble or transition metal or metal oxides as catalyst, and (b) relevant alcohol as substrate molecule for hydrogen and oxygenate generation.

In an embodiment, the present invention provides a process for the preparation of a photocatalyst device; wherein said process comprises the steps of:
  a. preparing a photocatalyst composite of titania and other metal by loading 1 wt % of other co-catalyst on titania by dry impregnation method; wherein the dry impregnation method comprises of taking titania and other metal separately in an alcohol solvent; sonicating them simultaneously for 10-15 mins; mixing the solution of other metal with titania solution and sonicating for 20-30 mins to obtain homogeneous dispersion of other metal on titania; finally drying the dispersion to solid at 55-60° C. for 10-12 hr to obtain dried catalyst;
  b. preparing uniform dispersion of the dried catalyst obtained in step (a) in an alcohol substrate and drop casting on a support to obtain the photocatalyst thin film device; or
  preparing uniform dispersion of the dried catalyst obtained in step (a) in an alcohol substrate and coating the dispersion over inner surfaces of a glass vessel, employing a rota-vapour method for 15 minutes and obtaining a thin layer of catalyst coated over the inner surfaces of the glass vessel and drying the catalyst coated glass vessel at 65° C. for 12 h to obtain the photocatalyst thin film device.

The other metal is noble or transition metal or metal oxides and is selected from palladium (Pd), Platinum (Pt), Gold (Au), Silver (Ag), Nickel (Ni), Cobalt (Co), Ruthenium (Ru), Cuprous oxide ($Cu_2O$), Titania ($TiO_2$) and Iron oxides. In particularly useful embodiment, metal is palladium.

The support is selected from glass plate, glass vessels/glass containers, indium tin oxide (ITO) glass plate, and a fluorine-doped tin oxide (FTO) glass plate, silicon wafer or steel. In particularly useful embodiment, support is glass plate and glass vessels.

The alcohol substrate is selected from primary alcohols, such as methanol, ethanol, secondary alcohols such as isopropanol, 2-butanol, and polyols, such as ethylene glycol, carbohydrates.

The photocatayst is in the form of a thin film present, generally, on the glass substrate. The ratio of weight of titania (in mg) to area of film (in $cm^2$) is in the range of 0.1 to 4 with preferred weight/area ratio of 0.0.2-0.25 $mg/cm^2$.

The film exhibits cracks and breaks and the film is drop casted on glass substrates, such as glass plates, inner surface of glass vessels.

Sunlight includes 4-5% of UV light; UV light, present in sunlight, in an amount of 25-50% is effectively converted to hydrogen by light to chemical conversion through water splitting.

The oxygenate products of primary, secondary and polyols include corresponding aldehyde, ketones and acids. Depending on the co-catalyst employed, the product can be a single or a mixture of the above oxygenated products.

DETAILED DESCRIPTION OF THE INVENTION

Figure 1:
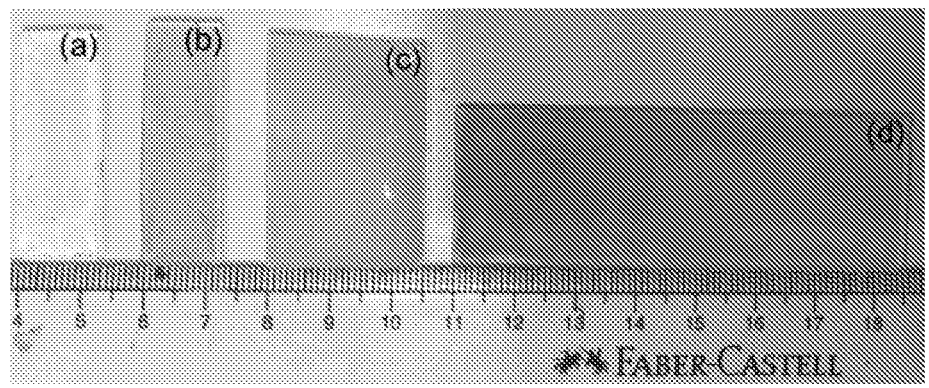
FIG. 1: Photographs of thin films of P25 of 1.25×3.75 $cm^2$ (a), and Pd/P25 of 1.25×3.75 $cm^2$ (b), 2.5×3.75 $cm^2$ (c), and 2.5×7.5 $cm^2$ (d)

The invention will now be described in detail in connection with certain preferred and optional embodiments, so that various aspects thereof may be more fully understood and appreciated.

While the invention is susceptible to various modifications and alternative forms, specific aspect thereof has been shown by way of examples and will be described in detail below. It should be understood, however that it is not intended to limit the invention to the particular forms disclosed, but on the contrary, the invention is to cover all modifications, equivalents, and alternative falling within the spirit and the scope of the invention as defined by the appended claims.

The terms "comprises", "comprising", or any other variations thereof, are intended to cover a non-exclusive inclusion, such that a composition, process that comprises a list of ingredients does not include only those ingredients but may include other ingredients not expressly listed or inherent to such composition or process. In other words, one or more elements in a product or process proceeded by "comprises . . . a" does not, without more constraints, preclude the existence of other elements or additional elements in the product or process.

The term "P25", wherever it appears in the whole body of description, is referred to titania. In line with the above objective, the present invention provides a photocatalyst device obtained by simple drop casting method for hydrogen generation using water splitting wherein commercial titania (P25; 3:1 anatase:rutile) is employed as the semiconductor to harvest direct sunlight and Pd is used as co-catalyst for $H_2$ generation by trapping electrons. Aqueous methanol or higher alcohols is used as sacrificial agent to scavenge the holes that are produced and thus to facilitate the efficient solar hydrogen production and aldehyde/acid. Pd/P25 and P25 are employed as the photocatalysts in both powder and panel type (thin film over glass plate) and compared the activities.

In an embodiment, the present invention provides a photocatalyst device obtained by simple drop casting method on flat surfaces or coating thin film on the inner-surfaces of glass vessels by rota-vapour method for generation of hydrogen and alcohol oxygenated products using water splitting; wherein said device comprises of (a) a titania photocatalyst, optionally in the form of composite with noble or transition metal or metal oxides, and (b) relevant alcohol substrate.

In an embodiment, the present invention provides a photocatalyst device obtained by simple drop casting process or coating thin film on the inner-surfaces of glass vessels by rota-vapour method; wherein said drop casting and rota-vapour process comprises the steps of:
  a. preparing a photocatalyst composite of titania and other metal co-catalyst by loading 1 wt % of other co-catalyst on titania by dry impregnation method; wherein the dry impregnation method comprises of taking titania and other metal separately in an alcohol solvent; sonicating for 10-15 mins; mixing the solution of other metal with titania solution and sonicating for 20-30 mins to afford homogeneous dispersion of other metal on titania; drying at 55-60° C. for 10-12 hr to obtain dried catalyst;
  b. preparing uniform dispersion of the dried catalyst obtained in step (a) in an alcohol substrate and drop casting on a support to obtain the photocatalyst thin film device; or
  dispersing the dried catalyst obtained in step (a) in alcohol substrate to obtain a suspension and coating the suspension over inner surfaces of a glass vessel, employing a rota-vapour method for 15 minutes and obtaining a thin layer of catalyst coated over the inner surfaces of the glass vessel and drying the catalyst coated glass vessel at 65° C. for 12 h to obtain the photocatalyst thin film device.

The other metal is noble or transition metal or metal oxides and is selected from palladium (Pd), Platinum (Pt), Gold (Au), Silver (Ag), Nickel (Ni), Cobalt (Co), Ruthenium (Ru), Cuprous oxide ($Cu_2O$), Titania ($TiO_2$) and Iron oxides. In particularly useful embodiment, metal is palladium.

The support is selected from glass plate, indium tin oxide (ITO) glass plate, a fluorine-doped tin oxide (FTO) glass plate, silicon wafer or steel. In particularly useful embodiment, support is glass plate.

The alcohol substrate is selected from primary alcohols, such as methanol, ethanol, and secondary alcohols such as isopropanol, 2-butanol, and polyols, such as ethylene glycol, carbohydrates.

The photocatayst is in the form of a thin film present on the surface of substrate or on inner surfaces of glass vessels.

The ratio of weight of titania (in mg) to area of film (in cm²) is in the range of 0.1 to 4 with optimum average weight/area ratio of 0.2-0.25 mg/cm².

The film exhibits cracks and breaks and the film is drop casted on a substrate. Possibly there are some discontinuous films observed, when coated on large area and that do not hamper the reaction. Optionally, the film can be prepared by spin-coating, sol-gel method, doctor-blade methods.

Sunlight includes 4-5% of UV light. UV light (present in sunlight) in an amount of 25-50% is effectively converted to hydrogen by light to chemical conversion through water splitting.

The present invention achieves much higher hydrogen production activities (~100 mmol/h/g) in thin film form, compared to conventional powder catalysts (~9 mmol/h/g) The oxygenated products of primary alcohols, secondary alcohols and polyols include corresponding aldehyde, ketones and acids. Depending on the co-catalyst metal employed, the product can be a single or a mixture of the above oxygenated products.

The photograph of thin films of the photocatalysts (P25, Pd/P25) is shown in FIG. 1. A colour difference is observed between the virgin (P25; white; FIG. 1a) and Pd/P25 (grey; FIGS. 1b, 1c and 1d) photocatalysts; (only 1.25×3.75 cm² area thin film is evaluated for the solar hydrogen production under direct sunlight in a quantitative manner). Photograph shown in FIG. 1 is mainly to demonstrate that bigger size films are also prepared by the drop-casting method. The appearance of all thin films suggests that the photocatalyst is not deposited uniformly over the glass plate and it is confirmed by FESEM analysis (shown later in FIG. 3). Nevertheless, the hydrogen evolution in the direct sunlight is visible over the entire film surface of 2.5×3.75 cm² tested. Even though the film surface exhibits inhomogeneity, gaps and cracks, the hydrogen generation is abundantly observed all over the surface. This is attributed possibly to the large penetration or skin depth of sunlight into the thin film of photocatalyst and possible internal reflection due to mesoporous texture of titania.

Figure 2:
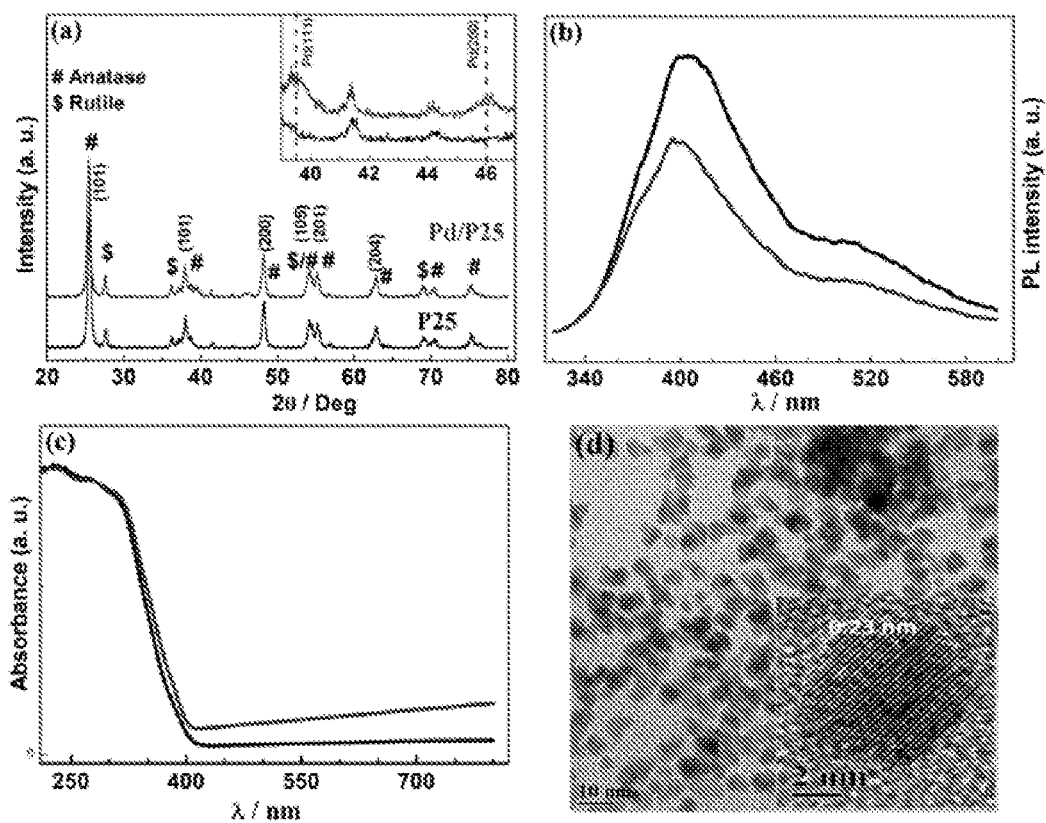
FIG. 2: Physical characterizations of P25 and Pd/P25 composite. (a) XRD patterns, and inset shows the enlarged view of Pd features, (b) Photoluminescence spectra, (c) UV-vis absorption spectra, and (d) TEM image of Pd nanoparticles and the inset shows the high resolution image of Pd nanoparticles.

The FIG. 2 presents the physical characterizations of P25 and Pd/P25. The structural details of photocatalysts are identified using XRD patterns (FIG. 2a). Rutile and anatase phase features are present in P25 and labelled to appropriate lattice planes; majority of the high intensity peaks are from anatase phase. The peaks observed at 2θ=39 and ~46° are of minor intensity corresponding to Pd(111) and Pd(200) facets, respectively (inset in FIG. 2a). FIG. 2b shows the PL characteristics of photocatalysts recorded with X, =310 nm photons. A relatively intense PL features with virgin P25 is observed suggest a high recombination rate of $e^-h^+$ pairs; On the other hand, Pd/P25 shows a significant attenuation of PL emission intensity; this demonstrate the electrons generated are trapped by Pd and thus provided an effective charge utilization for $H_2$ generation.

The UV-vis absorption spectra are given in FIG. 2c; as anticipated, P25 and Pd/P25 show strong absorption below 400 nm due to band gap excitation of predominant anatase titania. It is also observed that an increase in the background absorption of visible light for Pd/P25 is attributed to scattering of high wavelength light. This observation is consistent with grey color of the catalyst. Even though rutile phase is present, hardly there is any visible light absorption observed in FIG. 2c. TEM image of the Pd nanoparticles is presented in FIG. 2d. Size of Pd nanoparticles is between 3 and 5 nm with random morphology. The d-spacing measured from the lattice fringes is ~0.23 nm and it corresponds to the (111) lattice plane of Pd. It is to be noted that Pd(111) facet is further confirmed from XRD pattern (inset in FIG. 2a).

Figure 3:
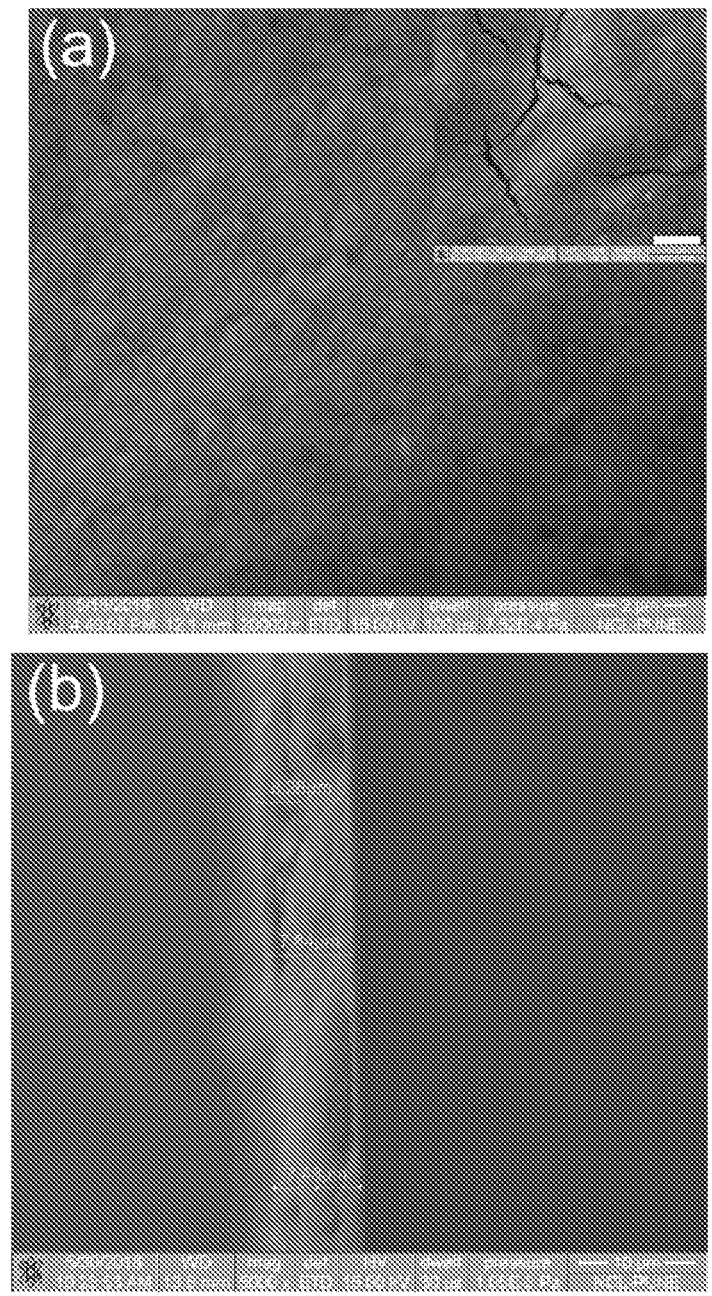
FIG. 3: FESEM images of Pd/P25 thin films over glass plate for (a) surface morphology at a scale bar of 2 μm, and (b) cross sectional view of freshly cleaved thin film at a scale bar of 10 μm. Inset in (a) shows the cracks present on the film surface at a scale bar of 10 μm.

The surface morphology, film thickness (FIG. 3) and composition details of the thin films are obtained using SEM with EDX set up. FIG. 3a suggests that the titania nanostructures are in good contact with each other. The cracks/gaps on the films are clearly visible (inset in FIG. 3a) suggesting the drop cast methodology need to be further improved to obtain the better quality films. Even though the inhomogeneity persists on thin film surface, very good hydrogen generation is observed from the entire thin film. EDX analysis of the Pd/P25 films provided the composition to be 0.91/56.47/42.63 wt % (Pd/Ti/O) and it is the same as that of the nominal input values. The average thickness of the film is measured to be 8 μm and it varies between 7.5 and 8.5 μm throughout the film (FIG. 3b).

Figure 4:
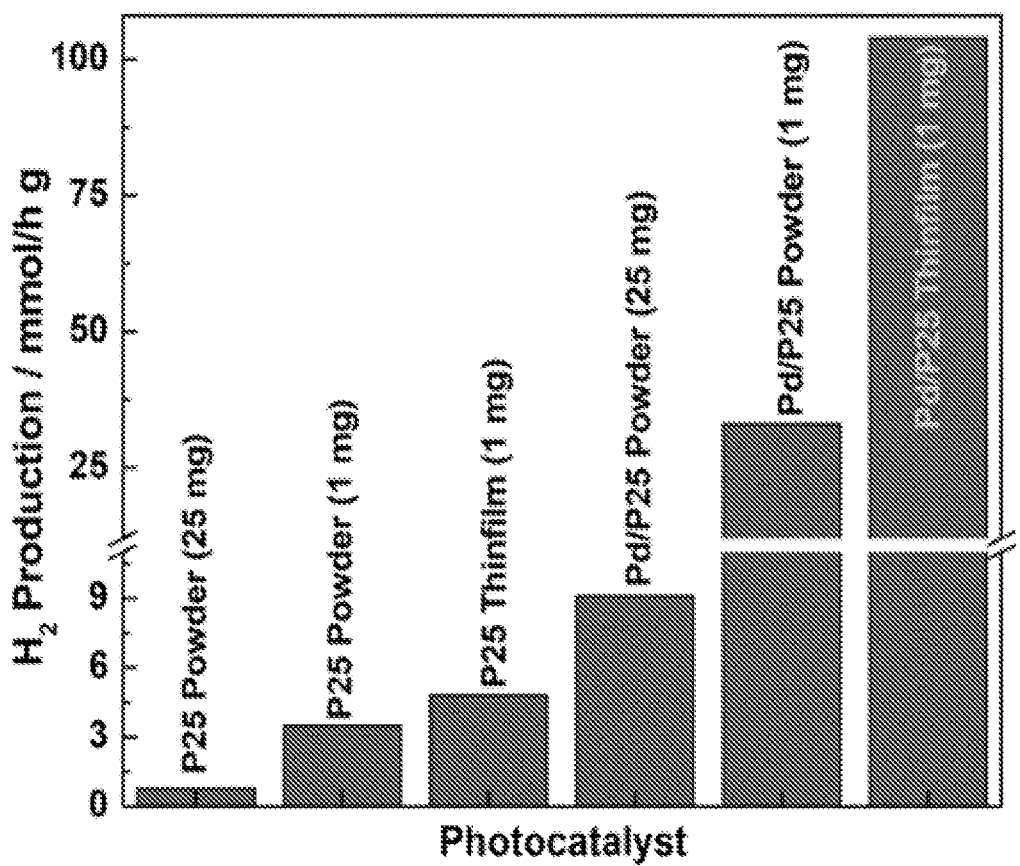
FIG. 4: Photocatalytic hydrogen production activities of P25 and Pd/P25: P25 powder (25 mg), P25 powder (1 mg), P25 thin film (1 mg), Pd/P25 powder (25 mg), Pd/P25 powder (1 mg), and Pd/P25 thin film (1 mg).

The hydrogen production activity of the catalysts in powder and thin film forms are evaluated under direct sunlight in the water/methanol mixture, and the results are shown in FIG. 4. The photocatalysts of powder form are evaluated by following the procedure reported in the literature [*Phys. Chem. Chem. Phys.*, 2015, 17, pp 19371-19378]. It is observed that the hydrogen production activities of powder catalysts (P25, Pd/P25) are low compared to the corresponding thin film form catalysts, even though catalyst remains the same. The small (1 mg) amount of catalyst in powder form always provide large amount of hydrogen, while large amount of catalyst (25 mg) lead to lower hydrogen yield. It is observed that P25 in the particulate form exhibits the lowest activity (0.76 mmol/h g) compared to its corresponding Pd/P25 composite counterpart (9.11 mmol/h g) tested with 25 mg photocatalyst. The most interesting observation is that 1 mg of powder form of Pd/P25 catalyst coated over 4.69 cm² shows the highest hydrogen production value of 104 mmol/h g. Further, it demonstrates that the phototcatalyst on the fixed substrate provide efficient photocatalytic reaction kinetics than that of powder form in solution. This maximizes the utilisation of surface area of Pd as well as P25. Among the catalysts, Pd/P25 exhibit better activity compared to virgin P25 suggesting Pd acts as a better co-catalyst to trap the electrons and increases hydrogen yield. It is to be noted that light absorption by anatase titania is only from UV and a marginal amount of visible light absorption occurs due to rutile up to 410 nm. Large $H_2$ generation underscores the necessity to exploit ~4% UV present in the sunlight. While powder form suffers from recombination, thin films overcome the same problem to a significant extent.

The experiments are carried out with 1 and 25 mg of powder $Pd/TiO_2$ under same conditions as that of other experiments. However, the solution is not stirred during illumination, mainly to simulate the thin film measurement conditions. No measurable $H_2$ generation is observed with 25 mg batch, while 1 mg batch shows 2.1 mmol/h·g. This suggests the stirring improves $H_2$ generation with minimum amount of catalyst, mostly due to better exposure to light; however the activity is far below the level of thin film made with 1 mg or powder under stirring. Thin film made with 2 mg (~14 μm thick) showed a mere 10% increase in activity than that of made with 1 mg.

The apparent quantum yield (AQY) of different catalysts is given in Table 1. The results suggest that virgin titania (P25) based catalyst exhibit negligible AQY compared to $Pd/TiO_2$. Among the catalysts tested, thin film based Pd/P25 has shown the highest AQY for solar hydrogen generation under direct sunlight.

TABLE 1

AQY of P25 and M/P25 (Pd, Pt, Au, Ag) in particulate
and thin film forms for solar hydrogen generation

| Catalyst (Weight) | AQY (%) |
|---|---|
| P25 powder (25 mg) | 0.007 |
| P25 powder (1 mg) | 0.032 |
| P25 thin film (1 mg) | 0.044 |
| Pd/P25 powder (25 mg) | 0.084 |
| Pd/P25 thin film (1 mg) | 0.96 |
| Pd/P25 powder (1 mg) | 0.31 |
| Au/P25 thin film (1 mg) | 0.84 |
| Ag/P25 thin film (1 mg) | 0.82 |
| Pt/P25 thin film (1 mg) | 0.35 |

The hydrogen production of Pd/P25 thin films at different loading of Pd is given in Table 2. Herein, the co-catalyst (Pd) is drop-casted on the surface of P25 film instead of mixing Pd with P25. The results suggest that less amount of Pd is sufficient to achieve the better hydrogen production activities compared to conventional method of prepared thin films and powder catalysts. Here two methods are investigated for hydrogen production. One is the mixing of Pd and P25 using sonication followed by drying and making thin film. Second, the deposition of Pd nanoparticles over P25 thin film and dried for 24 h before testing of them.

TABLE 2

Solar hydrogen activities at different
percentages of Pd of Pd/P25 thin films

| Quantity of Pd (wt %)[#] | H2 production (mmol/h/g) |
|---|---|
| Pd/P25 (1) | 87 |
| Pd/P25 (0.75) | 84 |
| Pd/P25 (0.5) | 106 |
| Pd/P25 (0.25) | 104 |
| Pd/P25 (0.125) | 80 |
| Pd/P25 (0.062) | 66 |
| Pd/P25 (0.025) | 37 |
| Pd/P25 (0.0125) | 14 |

[#]Pd is present in spherical morphology in the catalysts listed in table 2.

The formaldehyde activities are given in Table 3. The results suggest that virgin titania (P25) based catalyst exhibit no formaldehyde formation compared to Pd/TiO$_2$. Among the catalysts tested, thin film based Pd/P25 has shown better formaldehyde under direct sunlight. Quantification of formaldehyde (methanol oxygenated product) is done by using HPLC during the water splitting reaction in particulate and thin film form.

TABLE 3

Identification of formaldehyde for particulate and thin
films of different catalysts

| Catalyst (Weight)[#] | Irradiation time/h | Formaldehyde Yield (%) | Methanol conversion (%) |
|---|---|---|---|
| Without catalyst | 16 | 0 | 0 |
| P25 powder (25 mg) | 5 | 0 | 0 |
| P25 powder (1 mg) | 5 | 0 | 0 |
| P25 thin film (1 mg) | 5 | 0 | 0 |
| Pd/P25 thin film (1 mg) | 25 | 3 | 3 |
| Pd/P25 powder (1 mg) | 25 | 1.2 | 1.2 |
| PdPt/P25 thin film (1 mg) | 50 | 9 | 9 |

[#]Pd is in the form of truncated octahedron morphology.

EXAMPLES

The following examples, which include preferred embodiments, will serve to illustrate the practice of this invention, it being understood that the particulars shown are by way of example and for purpose of illustrative discussion of preferred embodiments of the invention.

Example 1: Synthesis of Pd Nanoparticles

The solution phase method was followed for the synthesis of 3-4 nm size Pd nanoparticles [*Nanotechnology;* 2016; 27(6):065603.]. In 25 mL round bottom flask (RBF), 105 mg of polyvinylpyrrolidone (PVP) and 60 mg of ascorbic acid (AA) was dissolved in 8 mL of distilled de-ionized (DDI) water using sonication and kept at 90° C. for 15 min. 60 mg of Potassium tetrachloropalladate(II) [K$_2$PdCl$_4$] dissolved in 3 mL of water using sonication followed by the addition to the host solution at 90° C. The reaction was continued for 3 h. After the reaction the solution was centrifuged, washed thoroughly with acetone and subsequently with ethanol/hexane mixture to collect Pd-nanoparticles.

Example 2: Synthesis of Pd/P25 Composite 1 wt % of Pd co-catalyst was loaded on titania (P25) by dry impregnation method and employed for testing of H$_2$ production activity. The desired amounts of P25 and Pd nanoparticles are taken in ethanol (20 mL) separately and sonicated for 15 min. After sonication, the Pd nanoparticle solution was added to the P25 nanoparticle solution and sonicated for further 30 min. for homogenous Pd dispersion on titania and kept for drying at 60° C. for 12 h.

Example 3: Preparation of Photocatalyst Thin Films Over Glass Plates

Initially, the glass plates of different sizes (1.25×3.75, 3.5×3.75, and 3.5×7.5 cm$^2$) were cleaned using soap solution, DI water and acetone under sonication for 45 min (each for 15 min) in sequential manner and kept at 65° C. for 3 h and used for thin film making. The drop casting methodology was adopted to prepare the thin films of the photocatalyst over the glass plates without addition of any binders. In 1 mL of ethanol, 1 mg of photocatalyst (P25 or Pd/P25) was added and sonicated for 30 min. to obtain uniform dispersion of the catalyst. This catalyst dispersion was drop casted repeatedly on the glass plate using 100 µl micropipette and dried under ambient conditions for 12 h.

a) Characterization of Thin Films:

The physical properties of virgin (P25) and Pd/P25 were explored by different characterization techniques. Powder X-ray diffraction (PXRD) data was collected from a PAN analytical X'pert Pro dual goniometer. Cu Kα (1.5418 Å) radiation with a Ni filter was employed as radiation source. Transmission electron microscope (TEM) images of materials were recorded using FEI TECNAI 3010 electron microscope operating at 200 kV and the images obtained were analysed using image J software. Photoluminescence (PL) measurements were conducted using Horiba Jobin Yuon Fluorolog 3 spectrophotometer equipped with a 450 W xenon lamp with a tuneable excitation wavelength. All PL measurements were taken at excitation pulses of 310 nm. To explore the light absorption properties UV-Visible spectroscopy was employed using a Shimadzu spectrometer (model UV-2550) with spectral-grade BaSO$_4$ as reference material. The morphological, composition, thickness details of the prepared films over glass plate are obtained using Quanta 200 3D field emission scanning electron microscope (FEG-SEM).

b) Testing of the Photocatalysts:

All photocatalysis experiments were carried out in direct sunlight, between 10 am and 4 pm on the terrace of National chemical laboratory (pune, India) premises. GPS location of Pune, India is 18.5204/73.8567/N 18 31' 14"/E 73 51' 24". Before measurement, the power of illuminated solar irradiance was measured using reference silicon solar cell and a read out meter for every hour of reaction and considered the average of it for calculation; it was 50.2 mW/cm$^2$. Powder and thin film forms of photocatalysts were subjected to solar hydrogen generation with 25% v/v aqueous methanol solution. In 70 mL quartz RBF, 25 mg powder catalyst was taken in 40 mL aqueous methanol and de-aerated with nitrogen for 30 min. This is followed by sonication for 15 min. to obtain uniform dispersion of the catalyst and RB was closed with air-tight septum. Same procedure was adopted for thin film catalyst. For reliable comparison of the H$_2$ production activities, 1 mg of powder catalyst was also tested by the same procedure; since 1 mg of catalyst was coated on the 1.25× 3.75 cm$^2$ glass substrate. The collected gas samples were analyzed periodically with an Agilent 7890A gas chromatograph (GC) equipped with a thermal conductivity detector at 200° C. The apparent quantum yield of solar hydrogen for all the catalysts was calculated by using the following equation;

$$AQY(\%) = \frac{2 \times \text{Number of hydrogen molecules}}{\text{Number of Incident photons}} \times 100$$

The number of incident photons was found to be 4% under natural sunlight and the amount calculated to be 3.6×10'$^8$ photons per sec from the contribution of up to ~410 nm; the light absorption by P25 and Pd/P25 is considered up to ~410 nm due to marginal visible light absorption by rutile phase titania.

c) Identification of Formaldehyde, Acetone, and Glycolaldehyde

High performance liquid chromatography (HPLC, Agilent technologies, modal 1250 infinity) was used to analyze the liquid samples for the identification of the methanol, isoproponal, ethylene glycol and those oxygenated products formed such as formaldehyde, acetone, and glycolaldehyde, respectively due to the photo oxidation. The formation of products was confirmed by matching experimental data with that of the standard samples. Liquid samples were analyzed using HPLC, equipped with RI detector (at 40° C.) and H$^+$ Aminex column (305 mm 7.8 mm) fitted with a guard column in series. Mobile phase used was 0.05M H$_2$SO$_4$ at a flow rate of 0.6 mL·min$^{-1}$ while maintaining the column temperature at 60° C.

Example 4: Optimization of Co-Catalyst Loading

As mentioned earlier, co-catalyst Pd is required to promote the water splitting reaction in the presence of methanol and thus to produce hydrogen with better yield. Though the reaction is feasible while using the Pd, the cost matters towards the cost-effective hydrogen production. Therefore, it is important to replace or effective utilization of expensive co-catalyst. Herein, we report a methodology that needs very less amount of co-catalyst (Pd) and thus decrease the cost of hydrogen production without compromising the activity. The known amount of colloidal Pd nanoparticle solution was drop-cast on the titania (P25) film and kept for drying for 24 h. The thin films were tested under sun light in the presence of water/methanol mixture. Thin films of different loading of co-catalyst (Pd) were tested for hydrogen production activity.

Example 5: Synthesis of Pd Nanocubes (Pd$_{NC}$)

The synthesis of the Pd nanocubes with dominant (100) facets are synthesized by following the example (1) except the use of potassium chloride (KCl) as a capping agent. The procedure is as follows. In 8 mL of water as solvent, 105 mg of PVP (poly vinyl pyrrolidone), 60 mg of Ascorbic acid, and 300 mg of KCl were added in 25 mL 3-neck round bottom flask (RBF), and kept at 90° C. under constant stirring. After five minutes, 3 ml of water containing 57 mg of K$_2$PdCl$_4$ was added to the above solution and kept at the same temperature (90° C.) for 3 h under constant stirring. After 3 h, the obtained brown-black colored nanoparticle solution was cooled to room temperature and collected in centrifuge bottles. The cleaning of the nanoparticles was carried out by centrifuging the solution one time with excess amount of acetone and three times with ethanol/hexane mixture (1:5 ratio) at 10,000 rpm for 10 minutes. The final precipitate was dispersed in water for further cleaning.

Example 6: Synthesis of Pd$_{NC}$/P25 Nanoparticles

For the preparation of Pd$_{NC}$/P25 of example (6), followed the same procedure of example (2) except the use of Pd$_{NC}$ nanoparticles instead of Pd.

Example 7: Preparation of Pd$_{NC}$/P25 Thin Films Over Glassplate

For the preparation of Pd$_{NC}$/P25 thin films over glassplate, followed the same procedure of example (3) except the use of Pd$_{NC}$/P25 instead of Pd.

Example 8: Testing of Pd$_{NC}$/P25 Thin Films

The testing of Pd$_{NC}$/P25 thin films followed the procedure of example (3(b)) and obtained the hydrogen production activity of 120 mmol/h/g.

Example 9: Synthesis of Pd Truncated Octahedra (Pd$_{TO}$)

The synthesis of the Pd truncated octahedral (Pd$_{TO}$) with dominant (111) facets are synthesized by following the example (1) except the use of citric acid as a capping agent [ref: Jin M., et al., Synthesis of Pd nanocrystals enclosed by {100} facets and with Sizes <10 nm for application in CO oxidation Nano Res., 2011, 4, 83-91].

Example 10: Synthesis of Pd$_{TO}$/P25 Nanoparticles

For the preparation of Pd$_{TO}$/P25 of example (10), followed the same procedure of example (2) except the use of Pd$_{TO}$ nanoparticles of example (9) instead of Pd nanoparticles of example (1).

Example 11: Preparation of Pd$_{TO}$/P25 Thin Films Over Glassplate

For the preparation of Pd$_{TO}$/P25 thin films over glassplate, followed the same procedure of example (3) except the use of Pd$_{TO}$/P25 of example (10) instead of Pd nanoparticles of example (1).

Example 12: Testing of $Pd_{TO}$/P25 Thin Films

The testing of $Pd_{TO}$/P25 thin films of example (12) followed the procedure of example (3(b)) and obtained the hydrogen production activity of 55 mmol/h/g.

Example 13: Synthesis of Half Monolayer Pt-Coated $Pd_{NC}$ (½Pt—$Pd_{NC}$)

To further demonstrate the effect of Pt deposition on facet engineered Pd nanoparticles towards solar hydrogen production, Pt-coated (half-a-monolayer) (from hereafter to be represented as ½Pt) counter-parts ($Pd_{NC}$) were synthesized following the procedure reported by R. K. Singh et al (Stability issues in Pd-based catalysts: the role of surface Pt in improving the stability and oxygen reduction reaction (ORR) activity, *Phys. Chem. Chem. Phys.*, 2013, 15, 13044-13051). The $NaBH_4$ reagent has been used to the formation of the hydrogen adsorbed ($Pd_{NC}$ hydride) nanoparticles. In 25 mL RBF, to the solution (10 mL) of $NaBH_4$-treated Pd nanoparticles, the desired amount of $K_2PtCl_4$ (half-a-monolayer of Pt over Pd of ~8 nm is 1:15 of Pt:Pd) dissolved in 5 mL of water was added and kept for sonication for 30 min. and thereafter kept at 70° C. under constant stirring for 12 h. The resulting solution was cleaned at room temperature with excess amount of water using centrifuge at 12000 rpm for 10 min. The final precipitate (Pt-coated counterparts; Pd—NCs, was collected and dried over night at 60° C. for further use.

Example 14: Synthesis of ½Pt—$Pd_{NC}$/P25 Nanoparticles

For the preparation of PdNC ½Pt—$Pd_{NC}$/P25 nanoparticles of example (14), followed the same procedure of example (2) except the use of ½Pt—$Pd_{NC}$/P25 nanoparticles of example (13) instead of Pd nanoparticles of example (1).

Example 15: Preparation of ½Pt—$Pd_{NC}$/P25 Thin Films Over Glassplate

For the preparation of ½Pt—$Pd_{NC}$/P25 thin films over glassplate, followed the same procedure of example (3) except the use of ½Pt—$Pd_{NC}$/P25 of example (14) instead of Pd nanoparticles of example (1).

Example 16: Testing of ½Pt—$Pd_{NC}$/P25 Thin Films

The testing of ½Pt—$Pd_{NC}$/P25 thin films of example (16) followed the procedure of example (3(b)) and obtained the hydrogen production activity of 110 mmol/h/g.

Example 17: Synthesis of Pt-Coated $Pd_{NC}$ (½Pt—$Pd_{TO}$)

For the preparation of ½Pt—$Pd_{TO}$, the procedure was followed same as that of example (13) except the use of $Pd_{TO}$ nanoparticles instead of $Pd_{NC}$.

Example 18: Synthesis of ½Pt—$Pd_{TO}$/P25 Nanoparticles

For the preparation of ½Pt—$Pd_{TO}$/P25 nanoparticles of example (18), followed the same procedure of example (2) except the use of ½Pt—$Pd_{TO}$/P25 nanoparticles of example (18) instead of Pd nanoparticles of example (1).

Example 19: Preparation of ½Pt—$Pd_{TO}$/P25 Thin Films Over Glassplate

For the preparation of ½Pt—$Pd_{TO}$/P25 thin films over glassplate, followed the same procedure of example (3) except the use of ½Pt—$Pd_{TO}$/P25 of example (18) instead of Pd nanoparticles of example (1).

Example 20: Testing of ½Pt—$Pd_{TO}$/P25 Thin Films

The testing of ½Pt—$Pd_{TO}$/P25 thin films of example (20) followed the procedure of example (3(b)) and obtained the hydrogen production activity of 130 mmol/h/g.

Example 21: Testing of Au/P25 Thin Films

The testing of Au/P25 thin films of example (21) followed the procedure of example (3(b)) and obtained the hydrogen production activity of 40 mmol/h/g.

Example 22: Testing of Ag/P25 Thin Films

The testing of Au/P25 thin films of example (22) followed the procedure of example (3(b)) and obtained the hydrogen production activity of 20 mmol/h/g.

Example 23: Testing of $Cu_xO$/P25 Thin Films

The testing of $Cu_xO$/P25 thin films of example (23) followed the procedure of example (3(b)) and obtained the hydrogen production activity of 58 mmol/h/g.

Example 24: Testing of Ni/P25 Thin Films

The testing of Ni/P25 thin films of example (24) followed the procedure of example (3(b)) and obtained the hydrogen production activity of 28 mmol/h/g.

Example 25: Testing of Co/P25 Thin Films

The testing of Co/P25 thin films of example (25) followed the procedure of example (3(b)) and obtained the hydrogen production activity of 18 mmol/h/g.

Example 26: Testing of Ru/P25 Thin Films

The testing of Co/P25 thin films of example (26) followed the procedure of example (3(b)) and obtained the hydrogen production activity of 75 mmol/h/g.

Example 27: Preparation of Thin Film of $Pd_{PC}$/P25 Catalyst Coated on the Inner-Surface of Glass Vessels (Total Volume: 300 mL)

Initially, 300 mL volume capacity glass vessel is cleaned as mentioned in example 3 and used for the catalyst coating on the inner side of the vessel. For this, in 25 mL of ethanol, 25 mg of prepared Pd/$TiO_2$ was dispersed and sonicated for 30 min. to obtain uniform suspension of the catalyst. In order to coat this catalyst over the inner surfaces of the glass vessel, we employed rota-vapour for 15 min. and obtained the thin layer of catalyst over the glass surfaces. The resultant catalyst coated glass vessel was kept for drying at 65° C. over night. The catalyst coated vessel was subjected to photocatalytic hydrogen production under direct sun light. Indeed, this procedure can be extrapolated to bigger vessels with required amount of catalyst for large scale hydrogen production.

Example 28: Preparation of Thin Film of $Pd_{PC}$/P25 Catalyst Coated on the Inner Surface of Small Glass Vessels (Total Volume: 70 mL)

We employed the same procedure as that of example (27) for coating the thin films over the inner surfaces of glass vessel of small size. The obtained thin film coated glass vessels are dried at 65° C. over night. The catalyst coated glass vessels were used for photocatalytic hydrogen generation under direct sunlight.

Example 29: Preparation of Thin Film of $Pd_{NC}$/P25 Catalyst Coated on the Inner Surface of Large Glass Vessels (Total Volume: 300 mL)

Procedure of example (27) was followed to obtain the inner coated thin film of $Pd_{NC}$/P25 in large glass vessel except the replacing $Pd_{PC}$/P25 catalyst with $Pd_{NC}$/P25.

Example 30: Preparation of Thin Film of $Pd_{NC}$/P25 Catalyst Coated on the Inner Surface of Small Glass Vessels (Total Volume: 70 mL)

Procedure of example (28) was followed to obtain the thin film of $Pd_{NC}$/P25 coated on the inner side of small glass vessel except the replacing $Pd_{PC}$/P25 catalyst with $Pd_{NC}$/P25.

Example 31: Testing of Thin Films of $Pd_{PC}$/P25 Catalyst Coated on the Inner Surface of Vessels for Solar Hydrogen (Total Capacity: 300 mL)

The thin films coated on the inner surfaces of glass vessel from the example (27) was subjected to hydrogen generation under direct sunlight. The glass vessel that coated with catalyst was filled with 200 mL of water/methanol mixture in which 25% (vol %) of methanol was presented. The vessel was closed with rubber septum. The vessel containing water/methanol mixture was de-aerated with nitrogen gas for 30 min to remove the dissolved oxygen in the solution. The vessel kept under sunlight from 11 am to 4 μm. The gas-phase product was analyzed using gas chromatography technique as mentioned in example 3 (b). The activity of the sample was 20 mmol/h/g

Example 32: Testing of Thin Film of $Pd_{PC}$/P25 Coated on the Inner Surfaces of Glass Vessel for Solar Hydrogen (Total Capacity: 70 mL)

The thin film coated on the inner surfaces of glass vessel (example (28)) was followed. Example of (31) was employed to cam out the reaction, except for filling with 40 mL of water/methanol mixture in which 25% (vol %) of methanol was present. The activity of the sample is found to be 12 mmol/h/g.

Example 33: Testing of Thin Films of $Pd_{NC}$/P25 Catalyst Coated on the Inner Surfaces of Glass Vessel for Solar Hydrogen (Total Capacity: 300 mL)

The testing of thin film that obtained from example (29) was employed with the reaction procedure described in example (31). The activity of the sample was found to be 45 mmol/h/g

Example 34: Testing of Thin Films of $Pd_{NC}$/P25 Catalyst Coated on the Inner Surfaces of Glass Vessel for Solar Hydrogen (Total Capacity: 70 mL)

The thin film obtained from the example (30) was employed to evaluate the catalytic activity with the procedure described in example (32). The activity of the sample is found to be 25 mmol/h/g.

Example 35: Identification of Formaldehyde for $Pd_{NC}$/P25 Thinfilms (Example (7))

The oxygenated product (formaldehyde) of the methanol has been identified for example (7) by repeating the procedure of example of (3(c)).

Example 36: Identification of Formaldehyde for $Pd_{TO}$/P25 Thinfilms (Example (11))

The oxygenated product (formaldehyde) of the methanol has been identified for example (11) by repeating the procedure of example of (3(c)).

Example 37: Identification of Formaldehyde for ½Pt—$Pd_{NC}$/P25 Thin Films (Example (16))

The oxygenated product (formaldehyde) of the methanol has been identified for example (16) by repeating the procedure of example of (3(c)).

Example 38: Identification of Formaldehyde for ½Pt—$Pd_{TO}$/P25 Thinfilms (Example (19))

The oxygenated product (formaldehyde) of the methanol has been identified for example (19) by repeating the procedure of example of (3(c)).

Example 39: Identification of Glycolaldehyde for $Pd_{NC}$/P25 Thinfilms

The oxygenated product (glycolaldehyde) of the ethylene glycol has been identified for example (8) by repeating the procedure of example of (3(c)). The conversion of ethylene glycol to glycolaldehyde is 5%.

Example 40: Identification of Acetone for $Pd_{NC}$/P25 Thinfilms

The oxygenated product (acetone) of the isopropanol has been identified for example (8) by repeating the procedure of example of (3(c)). The conversion of isopropanol to acetone is 3.8%.

Advantages of Invention

- The present invention provides a cost-effective way to generate hydrogen and alcohol oxygenated products via water splitting.
- Simple and cost-effective drop-cast methodology for the preparation of target thin films of different sizes
- Simple and cost effective rota-vapour method for coating thin film on the inner-surfaces of glass vessels.

Homogeneous hydrogen evolution from the entire film is obtained, even though film quality is not perfect and significant number of cracks/gaps persist Invention requires low material/equipments The present invention provided with much effective utilization of light because of light absorption instead of light scattering The thin film form of photocatalyst enables effective utilization of the photocatalyst (P25) and co-catalyst (Pd) towards better hydrogen production and formaldehyde The present invention achieves much better hydrogen production activities (~100 mmol/h/g) compared to conventional powder catalysts (~9 mmol/h/g)

Observed much better formaldehyde with thin film as methanol oxygenated product compared to powder form of the Pd/P25.

Number of co-catalysts can be employed to demonstrate the activity.

Many different alcohols can be used to make partially oxidized products, such as aldehyde, acid.

We claim:

1. A photocatalyst thin film device comprising;
a) a titania photocatalyst film in a form of a composite;
b) a support or glass vessels on which the titania photocatalyst film is deposited, wherein the support is selected from a glass plate, glass vessels, glass containers, an indium tin oxide (ITO) glass plate, and a fluorine-doped tin oxide (FTO) glass plate, a silicon wafer or steel; and
c) an aqueous alcohol substrate;
wherein the composite comprises the titania photocatalyst and a co-catalyst, wherein the co-catalyst is selected from the group consisting of a noble metal, a transition metal, a metal oxide and a combination thereof; and wherein a ratio of a weight of the titania, in mg, to an area of the film, in cm$^2$, is in a range of 0.1 to 4;
wherein the photocatalyst thin film device is configured to generate hydrogen and alcohol oxygenated products by splitting water in direct sunlight.

2. The photocatalyst thin film device as claimed in claim 1, wherein the device generates hydrogen corresponding to 25-50% of UV light from sunlight by light to chemical conversion through water splitting.

3. The photocatalyst thin film device, as claimed in claim 1, wherein the noble metal the transition metal or the metal oxide is selected from the group consisting of palladium, platinum, gold, silver, nickel, cobalt, ruthenium, cuprous oxide, titania and iron oxides.

4. The photocatalyst thin film device as claimed in claim 1, wherein the ratio of the weight of the titania, in mg, to the area of the film, in cm$^2$, is in a range of 0.2-0.25 mg/cm$^2$.

5. The photocatalyst thin film device as claimed in claim 1, wherein the film is drop casted on the surface of the support or coated over inner surfaces of the glass vessels and comprises cracks and breaks.

6. The photocatalyst thin film device as claimed in claim 1, wherein the aqueous alcohol substrate is selected from the group consisting of primary alcohols, secondary alcohols, and polyols; wherein the primary alcohols are selected from the group consisting of methanol and ethanol; wherein the secondary alcohols are selected from the group consisting of isoproponal and 2-butanol; and wherein the polyols are selected from the group consisting of ethylene glycol and carbohydrates.

7. The photocatalyst thin film device as claimed in claim 1, wherein the generated alcohol oxygenated products are formaldehyde and formic acid.

8. A process for preparation of a photocatalyst thin film device as claimed in claim 1, the process comprising:
loading 1 wt % of a co-catalyst on titania to prepare a photocatalyst composite, wherein the co-catalyst comprises a noble metal, a transition metal, or a metal oxide;
uniformly dispersing the photocatalyst composite in an aqueous alcohol substrate to obtain a catalyst dispersion;
placing the catalyst dispersion on a support to form the photocatalyst thin film device, wherein the support is selected from a glass plate, glass vessels, glass containers, an indium tin oxide (ITO) glass plate, and a fluorine-doped tin oxide (FTO) glass plate, a silicon wafer or steel; and
wherein a ratio of a weight of titania, in mg, to an area of the film, in cm$^2$, is in a range of 0.1 to 4.

9. The process as claimed in claim 8, wherein placing comprises drop casting the catalyst dispersion on the support or coating the catalyst dispersion over the support.

10. The process as claimed in claim 8, wherein preparing the photocatalyst composite comprises:
dry impregnating the titania and the co-catalyst by taking titania and the co-catalyst in an alcohol separately to obtain a solution of titania and a solution of the co-catalyst;
sonicating the solution of titania and the solution of the co-catalyst for 10-15 mins;
mixing the solution of the co-catalyst with the solution of titania and sonicating for 20-30 mins to form a uniform dispersion of the co-catalyst on titania; and
drying at a temperature in a range of 55-60° C. for 10-12 hour to obtain the photocatalyst composite.

11. The process as claimed in claim 9, further comprising drop casting the catalyst dispersion on the support to obtain the photocatalyst thin film device.

12. The process as claimed in claim 9, further comprising coating the catalyst dispersion over the inner surfaces of a glass vessel by employing a rota-vapour method for 15-60 minutes and obtaining a thin layer of the catalyst dispersion coated over the inner surfaces of the glass vessel and drying the catalyst dispersion coated glass vessel at a temperature in a range of 40-65° C. for 4-24 hour to obtain the photocatalyst thin film device.

13. The process as claimed in claim 8, wherein the noble metal, the transition metal, or the metal oxide is selected from the group consisting of palladium, platinum, gold, silver, nickel, cobalt, ruthenium, cuprous oxide, titania and iron oxides.

14. The process as claimed in claim 8, wherein the alcohol substrate is selected from the group consisting of primary alcohols, secondary alcohols, and polyols; wherein the primary alcohols are selected from the group consisting of methanol, ethanol; wherein the secondary alcohols are selected from the group consisting of isoproponal, 2-butanol; and wherein the polyols are selected from the group consisting of ethylene glycol, carbohydrates.

15. The process as claimed in claim 8, wherein the ratio of the weight of the titania, in mg, to an area of a film, in cm$^2$, of the photocatalyst thin film device is in a range of of 0.2-0.25 mg/cm$^2$.

16. The process as claimed in claim 8, wherein the film of the photocatalyst thin film device is drop casted on the support to exhibits cracks and breaks.

\* \* \* \* \*